United States Patent [19]

Mondet et al.

[11] Patent Number: 5,324,765

[45] Date of Patent: Jun. 28, 1994

[54] SURFACTANT CONTAINING COMPOSITION THICKENED WITH A COPOLYMER BASED ON AN ETHYLENICALLY UNSATURATED CARBOXYLIC ACID AND AN N-ALKYL ACRYLAMIDE

[75] Inventors: Jean Mondet, Drancy; Bertrand Lion, Livry-Gargan, both of France

[73] Assignee: L'Oreal, Paris, France

[21] Appl. No.: 56,774

[22] Filed: May 4, 1993

Related U.S. Application Data

[63] Continuation of Ser. No. 813,388, Dec. 27, 1991, abandoned.

[30] Foreign Application Priority Data

Dec. 27, 1990 [FR] France ............................ 90 16307

[51] Int. Cl.$^5$ ................................................ C08K 3/30
[52] U.S. Cl. .................................... 524/423; 524/156; 524/401; 524/555; 524/829; 524/831
[58] Field of Search ............... 524/423, 565, 831, 401, 524/156, 829

[56] References Cited

U.S. PATENT DOCUMENTS

| | | | |
|---|---|---|---|
| 4,423,199 | 12/1983 | Chang et al. | 524/555 X |
| 4,835,234 | 5/1989 | Valint et al. | 526/307.2 X |
| 4,882,405 | 11/1989 | Schulz et al. | 526/307.2 X |
| 5,021,526 | 6/1991 | Ball | 526/307.2 X |
| 5,037,863 | 8/1991 | Kozakiewicz et al. | 524/831 X |
| 5,102,936 | 4/1992 | Huth et al. | 524/555 X |

FOREIGN PATENT DOCUMENTS 0364887 4/1990 European Pat. Off. .
2180006 11/1973 France .

*Primary Examiner*—Judy M. Reddick
*Attorney, Agent, or Firm*—Cushman, Darby & Cushman

[57] ABSTRACT

A copolymer produced by the copolymerization of a monomer mixture comprising at least 30 weight percent of at least one organic ethylenically unsaturated carboxylic acid, at least 30 weight percent of at least one N-alkyl acrylamide the alkyl group of which contains 8 to 30 carbon atoms in the alkyl chain and 0 to 40 weight percent of at least one hydrophilic unsaturated monomer as well as a corresponding copolymer the carboxylic groups of which are completely or partially salified. The preparation and the use of the copolymer as a thickening agent in compositions having a high amount of a surfactant such as a shampoo are also disclosed.

18 Claims, No Drawings

SURFACTANT CONTAINING COMPOSITION THICKENED WITH A COPOLYMER BASED ON AN ETHYLENICALLY UNSATURATED CARBOXYLIC ACID AND AN N-ALKYL ACRYLAMIDE

This is a continuation of application Ser. No. 07/813,388, filed Dec. 27, 1991, now abandoned.

The present invention relates to new copolymers of N-alkyl acrylamide, their preparation and their use as thickening agents.

It is known that the salts of polymers produced by the polymerization of organic unsaturated carboxylic acids, such as the salts of polyacrylic and polymethacrylic acids, are employed as thickening agents in various aqueous systems.

The thickening of ionic surfactant solutions, for example, shampoo compositions, poses some particular problems. Thickening agents are very useful in such compositions since they impart unctuousness to the compositions. Moreover, thickening of surfactant solutions assists the use thereof by the consumer by avoiding a too large amount of the surfactant solution being poured out when the container housing the composition is tilted. Moreover, the thickening agent avoids or limits the decanting of certain ingredients present in the composition.

One of the most simple means for increasing the viscosity of anionic surfactant solutions is to add an electrolyte, generally a mineral salt such as sodium chloride or ammonium chloride.

However, mineral salts generally cannot be employed as the only thickening agent because that would require a too large amount which would be incompatible with certain uses.

One of the disadvantages of polymers derived from unsaturated carboxylic acids is that they are incompatible with mineral salts. For example, systems thickened with such polymers have a viscosity which is greatly decreased when an electrolyte, such as sodium chloride, is added; see, for example, U.S. Pat. No. 4,423,199.

In U.S. Pat. No. 4,423,199, the use of unsaturated carboxylic acid polymers, modified by the presence of other comonomers is contemplated and in particular derivatives of N-alkyl acrylamide having a long alkyl chain.

The only copolymers specifically described in this U.S. patent are produced from comonomer mixtures containing 5 weight percent of a long chain N-alkyl acrylamide. The specification indicates that the starting comonomer mixture can contain from 0.5 to 25 weight percent of N-alkyl acrylamide and preferably from 1 to 15 weight percent.

The copolymer thickeners described in this U.S. patent can be employed in the presence of surfactants, generally up to a concentration of 2.5 percent of surfactants, the useful amount of surfactants being, according to this patent, between about 0.1 and 1.0 weight percent.

One of the disadvantages of the copolymers described in U.S. Pat. No. 4,423,199 is that their thickening effect reaches a maximum and then decreases proportionately as the amount of surfactant increases.

The copolymers described in this U.S. patent are not suitable to thicken media in which the surfactant concentration is sufficiently high. This is the case, for example, with certain cosmetic compositions, such as shampoos, for which the surfactant concentration is generally greater than 5 weight percent. In effect, with the copolymers effectively described in U.S. Pat. No. 4,423,199 (containing 5 percent of N-alkyl acrylamide units), the viscosity is certainly increased for weak surfactant concentrations, between 0.1 and 3 weight percent, but this viscosity again becomes very weak for higher surfactant concentrations, even in the presence of a mineral electrolyte concentration greater or equal to 1 weight percent in the solution.

Also by using copolymers, such as those envisaged by U.S. Pat. No. 4,423,199, containing from 20 to 25 weight percent of N-alkyl acrylamide units, it is possible to increase the viscosity of certain surfactants in solution, such as sodium lauryl sulfate at a concentration of 8 percent, but the texture of the resulting gels is too stringy on discharge and is not therefore practically suitable.

It has no been discovered that it is possible to thicken media containing one or more surfactants at a concentration greater than or equal to 5 weight percent, by employing new copolymers containing, in addition to units derived from organic unsaturated carboxylic acids, at least 30 weight percent of units derived from long chain N-alkyl acrylamide.

The present invention thus relates to a copolymer characterized by the fact that it is produced by the copolymerization of a monomer mixture comprising:

at least 30 weight percent of at least one organic ethylenically unsaturated carboxylic acid;

at least 30 weight percent of at least one N-alkyl acrylamide wherein the alkyl moiety contains from 8 to 30 carbon atoms in the alkyl chain;

and from 0 to 40 weight percent of a hydrophilic unsaturated monomer.

The copolymer of the present invention can be partially or totally salified.

The mixture of monomers employed to prepare the copolymer of the invention also can exhibit the following characteristics, taken singly or in combination:

the said organic ethylenically unsaturated carboxylic acid is selected from acrylic acid and methacrylic acid;

the said alkyl group of the N-alkyl acrylamide contains from 8 to 16 carbon atoms and, in particular, from 8 to 12 carbon atoms, the said hydrophilic unsaturated monomer is, preferably, nonionic; it is a question, for example, of acrylamide;

the said monomer mixture contains from 30 to 60 weight percent of an organic ethylenically unsaturated carboxylic acid;

the said monomer mixture contains from 30 to 50 weight percent of N-alkyl acrylamide; and the said monomer mixture contains from 0 to 25 weight percent of said hydrophilic monomer.

The measurement of the molecular mass of the copolymers of the invention is not routinely attainable. It is known that the viscosity of polymer solutions increases with the molecular mass. For practical reasons, there will preferably be employed, according to the invention, copolymers such as defined above, of which a 1 weight percent aqueous solution containing 5 percent sodium lauryl sulfate and 1 percent sodium chloride and in which the copolymer is totally neutralized by 2-amino-2-methyl propanol, has a viscosity at least equal to 0.3 Pa.s (at 25° C.). The viscosity is measured, for example, with a Couette viscosimeter. Principally the apparatus sold by Contraves under the trade name "RHEOMAT" is employed.

This practical definition is the preferred lower limit of the viscosity which is then equivalent to that of the preferred lower limit of the molecular mass for the copolymer of the invention.

There is not, theoretically, an upper limit to the molecular mass other than limits inherent in the preparation process employed and other than those flowing from the necessity of being able to solubilize the copolymer at least partially neutralized in the aqueous solution containing at least 5 percent of surfactant.

The invention also relates to a process for the preparation of a copolymer such as defined above. This process comprises, principally, mixing in the requisite amounts, at least one organic ethylenically unsaturated carboxylic acid, at least one N-alkyl acrylamide the N-alkyl group of which contains from 8 to 30 carbon atoms in the chain, and optionally a hydrophilic unsaturated monomer. The resulting mixture is then submitted to a copolymerization reaction in accordance with known methods.

The polymerization process can be carried out in accordance with a radical chain growth polymerization reaction in the presence of an initiator such as azo-bis-isobutyronitrile.

The preparation of the copolymers of the invention can also be effected in accordance with an emulsion polymerization reaction. Mention can be made, in particular, of direct emulsion polymerization processes or inverse emulsion processes (of the water-in-oil type); "micellar" polymerization processes, that is to say, in an aqueous solution in the presence of a surfactant in an amount sufficient to solubilize the hydrophilic monomer (N-alkyl acrylamide); and precipitation or dispersion polymerization processes in an organic solvent. These processes are known in themselves. In the dispersion or precipitation polymerization processes, the organic solvent employed is a solvent for the monomers as well as a precipitant of the polymer in proportion of its formation. These latter processes are particularly well adapted to the synthesis of the copolymer of the invention and lead to molecular weights sufficient for the thickening of the media such as shampoos containing significant amounts of surfactants. The viscosity of the copolymers of the invention increasing with their molecular mass, it is in effect desirable to obtain products of high molecular mass in order to limit the amount of the copolymer added to the solution to be thickened. For example, in the case of a shampoo, it is preferable only to use the copolymer in an amount lower than or equal to 5 weight percent relative to the total weight of the composition, and preferably lower than or equal to 2 weight percent.

The copolymers of the invention prepared by dispersion or precipitation polymerization in an organic solvent are obtained in powder form which is easy to decant, to wash and to dry.

To obtain good dissolution of these copolymers in the aqueous solutions containing at least 5 percent of a surfactant, the copolymers of the invention are suspended in the solution and then partially or totally neutralized by a mineral or organic base. In effect, for use as a thickening agent, the carboxylic groups present in the units derived from the organic unsaturated carboxylic acid monomer must be at least partially salified, the degree of neutralization (salification) being sufficient so that the partially salified polymer is soluble in the medium used. In practice, the degree of neutralization necessary to obtain a dissolution of the copolymer under the use conditions mentioned above is always greater than 50 percent. Among the mineral bases employed for the salification mention can be made, in particular, of sodium hydroxide, potassium hydroxide and ammonia. Among the useful organic bases for this salification, mention can be made, in particular, of amino alcohols, such as 2-amino-2-methyl propanol, triethanolamine and triisoproanolamine.

The copolymers of the invention can be employed in the preparation of thickened aqueous surfactant solution compositions, which constitute, principally, shampoo compositions.

The surfactant agent is principally an anionic surfactant. There can be mentioned, for example, in a non-limiting manner, the alpha-olefin sulfonates, as well as alkyl sulfonates such as sodium lauryl sulfate, ammonium lauryl sulfate, triethanolamine lauryl sulfate and sodium laurylether sulfate; carboxyl containing alkanols, sulfosuccinates, alkylsarcosinates and isothionates.

The surfactants can also be nonionic surfactants. In particular, mention can be made of polyoxyethylenated fatty alcohols, polyglycerolated fatty alcohols, polyglycerolated N-alkylamides and glycoside or polyglycoside alkyl ethers or alkyl esters, oxyethylenated sterols and oxyethylenated phytosterols.

The useful surfactants can also be of an amphoteric nature; mention can be made, in particular, of the alkyl-betaines and the alky amidobetaines.

Certainly, the composition to be thickened can contain mixtures of surfactants belonging, optionally, to various classes.

The invention also relates to the use of, as a thickening agent, a copolymer such as defined above, in an aqueous composition containing at least 5 weight percent of a surfactant, principally an anionic surfactant.

The aqueous composition can also contain a mineral electrolyte.

The invention principally concerns the use of the copolymer as a thickening agent in an aqueous composition containing the surfactant and at least 0.5 percent of a mineral electrolyte.

The invention extends to thickened aqueous compositions thus obtained.

The mineral electrolyte is, for example, a salt such as sodium chloride, sodium sulfate, magnesium sulfate, etc.

The presence of the mineral electrolyte, preferably sodium chloride, permits to obtain a significantly better thickening effect in the surfactant solution containing the polymer.

It has been noted that the added mineral electrolyte also permits to modify the texture of the thickened composition, and in particular to avoid a stringy appearance during discharge.

The copolymers of the invention can also be employed to produce stable dispersions of nonmiscible liquid cosmetic materials such as silicone oils and/or gums, mineral oils or vegetable oils.

The resulting thickener can also be employed to maintain, in suspension, solid substances used in cosmetics, such as clays, opacifiers or silicone powders.

In addition to the mineral electrolyte, water soluble organic salts can be added, if desired. Mention can be made, for example, of sodium citrate, sodium or ammonium xylene sulfonate, or even a sunscreen agent (ultraviolet absorber) having a sulfonate unit.

As indicated above, the thickened composition of the invention contains at least one surfactant (at least 5 percent and generally from 5 to 15 weight percent) and optionally at least one mineral electrolyte. The thickened composition contains from 0.5 to 5 percent, and, in particular, from 0.5 to 2 weight percent of the copolymer. The mineral electrolyte is preferably present, in the thickened composition, in an amount at least equal to 1 weight percent and generally between 1 and 2.5 weight percent.

Such a composition constitutes principally a shampoo composition and can contain, optionally, other conventional cosmetic agents employed in shampoos.

If desired, the pH of the thickened solution can be adjusted using an appropriate base, generally between 5 and 9 and preferably between 5 and 7.5.

The following nonlimiting examples illustrate the invention.

Preliminary Examples: Preparation of Starting Products

Synthesis of N-octylacrylamide

In a reactor containing 0.5 mole of octylamine, 0.5 mole of triethylamine, 1 g hydroquinone monomethyl ether and 800 ml of toluene, 0.5 mole of acryloyl chloride in 200 ml is slowly introduced with stirring. The temperature is maintained at 25° C. by cooling during the duration of the addition (1 hour). The reaction is carried out for 24 hours at 25° C. with stirring. The triethylamine hydrochloride formed is then removed by filtration and the toluene is evaporated under reduced pressure. The resulting product is purified by distillation under a vacuum with recovery of the fraction distilling over at a temperature between 126° and 130° C. under 0.7 mbars. A colorless viscous liquid is obtained, the structure of which has been confirmed by NMR$^1$H. Yield: 70%.

Synthesis of N-dodecylacrylamide

The preceding procedures have been repeated except that the octylamine is replaced by dodecylamine; only the purification differs. After filtration of the triethylamine hydrochloride, the organic phase is washed with water. The toluene phase is then concentrated under a vacuum, diluted with 1 liter of petroleum ether and then subjected to cold crystallization. A waxy white solid is obtained whose structure has been confirmed by NMR$^1$H. Yield: 85%.

EXAMPLE 1

There are successively introduced into a reactor 15.5 g of acrylic acid, 14.2 g of acrylamide and 20.3 g of N-dodecylacrylamide. 300 g of methyl acetate as solvent for the monomers and precipitant of the polymer are added together with 1 g of azobisisobutyronitrile. The mixture of monomers is dissolved, with stirring and nitrogen bubbling, by heating until boiling (57° C.). The formed polymer precipitates in the medium under stirring in proportion to its formation and the reaction is carried out at 57° C. for 18 hours under these conditions.

After returning to ambient temperature, the polymer in suspension is filtered under a vacuum, washed twice on fritted glass with 300 ml of ethyl acetate, recovered and oven dried at 50° C. under a vacuum to a constant weight. The yield obtained after drying is 94%.

EXAMPLES 2 TO 9

In these examples 50 g of the monomer mixture are employed under synthesis conditions analogous to those of Example 1. The monomer solvent and the formed polymer precipitant is always methyl acetate except in Example 5 where 1,2-dichloroethane is employed for the polymerization (300 g) and for the consecutive washings. In this latter case (Example 5) the reaction is carried out at 65° C. To maintain a medium sufficiently stirrable during the polymerization, it is necessary, however, to add 300 g of solvent after 1 hour of reaction: this is the case for Examples 2, 4, 6 and 9. The results are given in the Table I, below. The structure of the resulting polymers is confirmed by NMR$^1$H.

TABLE I

| Example No. | Weight Percent of the Monomers | | | | | Yield |
|---|---|---|---|---|---|---|
| | AA | AM | A | DA | OA | |
| 2 | 42.9 | — | 18.1 | — | 39 | 95% |
| 3 | 22.3 | 20.2 | 17.8 | 39.2 | — | 94% |
| 4 | 38.4 | — | 16.2 | 45.4 | — | 91% |
| 5 | 59.5 | — | — | 40.5 | — | 87% |
| 6 | 48.8 | — | 10.7 | 40.5 | — | 93% |
| 7 | 49.5 | — | 19.3 | 31.2 | — | 93% |
| 8 | 41 | — | 18.4 | 40.6 | — | 91% |
| 9 | 45.3 | — | 20.4 | — | 34.3 | 92.4% |

AA: acrylic acid
AM: methacrylic acid
A: acrylamide
DA: N-dodecylacrylamide
OA: N-octylacrylamide Study of the Thickening Effect (a) Example of the formulation of a gel with the polymer of Example 1 in ethoxylated sodium lauryl sulfate (sodium lauryl ether sulfate).

The amounts of reactants are the following for a 100 g formulation.

Polymer No. 1 - 1 g (1 weight percent); 2-amino 2-methyl propanol for total neutralization of the carboxylic units of the polymer - 383 mg; ethoxylated sodium lauryl sulfate - 8 g (in active material); sodium chloride in a variable amount (see below); permutted water, sufficient amount for 100 g.

The dissolution of the reactants is effected by stirring at 70° C. for 24 hours. Table II, below, sets forth the results of viscosity (measured with a Contraves viscosimeter at 25° C.) and texture of the gels obtained as a function of the percent of sodium chloride in the mixture.

TABLE II

| % NaCl | Viscosity, in Pa · s. | Texture of the gel |
|---|---|---|
| 0 | 0.25 | — |
| 1 | 0.49 | — |
| 1.5 | 1.00 | Ropy or stringy texture |
| 2 | 3.0 | Correct texture on pouring or discharge |

It is considered that a gel exhibits a correct texture when it can flow and that it flows without being ropy. It must be neither brittle nor elastic. Its texture has the appearance of that of a cream.

This example shows the effect of the salt on the viscosity and the texture of the gel. In this given case a satisfactory result is only obtained with 2 percent of the salt.

When used as a capillary shampoo, the comparison of the formulation containing 2 percent sodium chloride to a solution of the surfactant without the polymer is characterized by better foam formation, better spreading on the hair, a more creamy appearance, a more constant foam, greater softness, more agreeable feel, and greater lightness on moist hair, and on dry hair by greater softness and more agreeable feel, without interfering with lightness.

(b) Thickening of a 10% sodium lauryl sulfate solution in the presence of 1% sodium chloride The various polymers of Examples 1 to 9 are compared as thickeners using the same surfactant solution containing: 1 g of polymer; 2-amino-2-methyl propanol in an amount corresponding to the complete neutralization of the polymer: 1 g of sodium chloride; 10 g of sodium lauryl sulfate; and permutted water in an amount sufficient for 100 g. The results of the viscosity measurements (Contraves at 25° C.) are set forth in Table III, below.

TABLE III

| Polymer of Example | Viscosity, Pa · s. |
|---|---|
| No. 1 | 3.40 |
| No. 2 | 4.07 |
| No. 3 | 3.02 |
| No. 4 | 2.45 |
| No. 5 | 1.12 |
| No. 6 | 7.00 |
| No. 8 | 6.00 |
| No. 9 | 2.80 |

(c) Comparison of the thickening effect with various surfactants

1. Anionic surfactants

Aqueous solutions are prepared containing a surfactant sodium chloride and a polymer according to the invention.

In all cases, the polymer dry extract is 1 percent, and the polymer is completely neutralized by 2-amino-2-methyl propanol.

The amount and the viscosity of the solutions studied are set forth in Table IV below.

TABLE IV

| Polymer of Example No. | Surfactant | % of Surfactant | % of NaCl | Viscosity (Pa · s.) |
|---|---|---|---|---|
| 1 | Sodium lauryl sulfate | 10 | 0 | 0.44 |
| | Sodium lauryl sulfate | 10 | 1 | 3.40 |
| | Sodium lauryl ether sulfate | 8 | 0 | 0.25 |
| | Sodium lauryl ether sulfate | 8 | 1 | 0.49 |
| | Sodium lauryl ether sulfate | 8 | 2 | 3.00 |
| | Triethanolamine lauryl sulfate | 10 | 0 | 0.45 |
| | Triethanolamine lauryl sulfate | 10 | 1 | 0.95 |
| | Triethanolamine lauryl sulfate | 10 | 2 | ≧3.00 |
| No. 8 | Sodium lauryl sulfate | 10 | 0 | 0.35 |
| | Sodium lauryl sulfate | 10 | 1 | 6.00 |
| | Sodium lauryl ether sulfate | 8 | 0 | 0.13 |
| | Sodium lauryl ether sulfate | 8 | 1 | 0.40 |
| | Triethanolamine lauryl sulfate | 10 | 0 | 0.31 |
| | Triethanolamine lauryl sulfate | 10 | 1 | 1.20 |
| | Triethanolamine lauryl sulfate | 10 | 2 | 3.00 |

Sodium lauryl ether sulfate, oxyethylenated with 2.2 moles of ethylene oxide, is that sold by Henkel under the trade name "SIPON A05-225".

2. Amphoteric surfactant

The surfactant is the cocodimethylsulfopropyl betaine described in the CTFA dictionary under the name "coco-sultaine". The concentration of polymer is 1.5 percent and the acid functions are completely neutralized by 2-amino-2-methyl propanol. The surfactant is used at a concentration of 10 percent. The results are the following (Table V)

TABLE V

| Polymer of Example | % NaCl | Viscosity (Pa · s.) |
|---|---|---|
| No. 8 | 1 | 2.0 |
| No. 8 | 2 | 1.4 |

3. Nonionic surfactant

The surfactant is 1,2-dodecanol etherified by 3.5 units of glycerol described in French patent 2.091.516 (71.17206). The polymer concentration is 1.5 percent. The polymer is completely neutralized by 2-amino-2-methyl propanol. The concentration of the surfactant is 10 percent. The results are set forth in Table VI below.

TABLE VI

| Polymer of Example | % NaCl | Viscosity (Pa · s.) |
|---|---|---|
| 2 | 1 | 1.40 |
| 2 | 2 | 1.25 |
| 8 | 1 | 0.28 |
| 8 | 2 | 7.00 |

We claim:

1. An aqueous composition containing at least 5 weight percent of at least one surfactant and further comprising, as a thickening agent, at least one copolymer resulting from the copolymerization of a monomer mixture comprising at least 30 weight percent of at least one ethylenically unsaturated carboxylic acid, at least 30 weight percent of at least one N-alkyl acrylamide wherein the alkyl group contains 8 to 30 carbon atoms in the alkyl chain, and from 0 to 40 weight percent of at least one non-ionic hydrophilic unsaturated monomer, the said copolymer being at least partially salified and being present in an amount ranging from 0.5–5.0 weight percent based on the total weight of said composition.

2. The composition of claim 1 wherein said ethylenically unsaturated acid is acrylic acid or methacrylic acid.

3. The composition of claim 1 wherein the alkyl group of the said N-alkyl acrylamide contains from 8 to 16 carbon atoms.

4. The composition of claim 1 wherein the alkyl group of the said N-alkyl acrylamide contains from 8 to 12 carbon atoms.

5. The composition of claim 1 wherein said hydrophilic unsaturated monomer is acrylamide.

6. The composition of claim 1 wherein said monomer mixture contains from 30 to 60 weight percent of said ethylenically unsaturated carboxylic acid.

7. The composition of claim 1 wherein said monomer mixture contains from 30 to 50 weight percent of said N-alkyl acrylamide.

8. The composition of claim 1 wherein said monomer mixture contains from 0 to 25 weight percent of said hydrophilic unsaturated monomer.

9. The composition of claim 1 wherein said copolymer is completely salified.

10. The composition of claim 1 wherein said copolymer is at least 50 percent salified.

11. The composition of claim 1 wherein said surfactant is an anionic surfactant.

12. The composition of claim 1 wherein said copolymer is present in an amount ranging from 0.5 to 2 weight percent based on the total weight of said composition.

13. The composition of claim 1 which also contains a mineral electrolyte.

14. The composition of claim 13 wherein said mineral electrolyte is present in an amount of at least 0.5 weight percent based on the total weight of said composition.

15. The composition of claim 13 wherein said mineral electrolyte is a salt.

16. The composition of claim 15 wherein said salt is selected from the group consisting of sodium chloride, sodium sulfate and magnesium sulfate.

17. The composition of claim 15 wherein said salt is present in an amount of at least 1 percent based on the total weight of said composition.

18. An aqueous composition comprising at least 5 weight percent of at least one surfactant and, as a thickening agent, at least one copolymer resulting from the copolymerization of a monomer mixture comprising 30 to 60 weight percent of at least one ethylenically unsaturated carboxylic acid, 30 to 50 weight percent of at least one N-alkyl acrylamide wherein the alkyl group contains 8 to 30 carbon atoms in the alkyl chain and from 0 to 25 weight percent of at least one hydrophilic unsaturated monomer, the said copolymer being at least partially salified.

* * * * *